(12) United States Patent
Payne et al.

(10) Patent No.: US 7,511,129 B2
(45) Date of Patent: Mar. 31, 2009

(54) ***BACILLUS THURINGIENSIS* ISOLATE ACTIVE AGAINST LEPIDOPTERAN PESTS, AND GENES ENCODING NOVEL LEPIDOPTERAN-ACTIVE TOXINS**

(75) Inventors: Jewel Payne, San Diego, CA (US); August J. Sick, Oceanside, CA (US)

(73) Assignee: Mycogen Corporation, Indianapolis, IN (US)

( * ) Notice: Subject to any disclaimer, the term of this patent is extended or adjusted under 35 U.S.C. 154(b) by 20 days.

(21) Appl. No.: 11/601,345

(22) Filed: Nov. 17, 2006

(65) Prior Publication Data

US 2007/0118924 A1 May 24, 2007

Related U.S. Application Data

(60) Division of application No. 10/825,751, filed on Apr. 16, 2004, now Pat. No. 7,138,568, which is a division of application No. 09/837,961, filed on Apr. 19, 2001, now Pat. No. 6,737,273, which is a division of application No. 09/521,344, filed on Mar. 9, 2000, now Pat. No. 6,573,240, which is a division of application No. 08/933,891, filed on Sep. 19, 1997, now Pat. No. 6,096,708, which is a continuation of application No. 08/356,034, filed on Dec. 14, 1994, now Pat. No. 5,691,308, which is a continuation of application No. 08/210,110, filed on Mar. 17, 1994, now abandoned, which is a continuation of application No. 07/865,168, filed on Apr. 9, 1992, now abandoned, which is a division of application No. 07/451,261, filed on Dec. 14, 1989, now Pat. No. 5,188,960, which is a continuation-in-part of application No. 07/371,955, filed on Jun. 27, 1989, now Pat. No. 5,126,133.

(51) Int. Cl.
*C07H 21/04* (2006.01)
*C12N 5/10* (2006.01)
*C07K 14/00* (2006.01)

(52) U.S. Cl. ............... 536/23.1; 530/350; 435/325; 435/235.1

(58) Field of Classification Search ............... 536/23.1; 530/350; 435/325, 235.1
See application file for complete search history.

(56) References Cited

U.S. PATENT DOCUMENTS

| 5,126,133 | A | 6/1992 | Payne et al. |
| 5,164,180 | A | 11/1992 | Payne et al. |
| 5,188,960 | A | 2/1993 | Payne et al. |
| 5,206,166 | A | 4/1993 | Payne et al. |
| 5,246,852 | A | 9/1993 | Payne et al. |
| 5,407,825 | A | 4/1995 | Payne et al. |
| 5,691,308 | A | 11/1997 | Payne et al. |
| 6,096,708 | A | 8/2000 | Payne et al. |

FOREIGN PATENT DOCUMENTS

| AU | 0632335 | 5/1993 |
| EP | 0 400 246 | 5/1990 |

OTHER PUBLICATIONS

Schnepf et al., J. Biol. Chem. 260, 6264-6272 (1985).*
Shibano et al., Gene 34, 243-251 (1985).*
U.S. Appl. No. 08/087,388, Gawron-Burke et al.
Chambers et al., "Isolation and Characterization of a Novel Insecticidal Crystal Protein Gene from . . . ," Journal of Bacteriology, 1991, pp. 3966-3976, vol. 173, Issue 13.
Hofte et al., "Nucleotide sequence and deduced amino acid sequence of a new Lepidoptera-specific crystal protein gene . . . ," Nucleic Acids Research, 1990, p. 5545, vol. 18.
Honée et al., "Nucleotide sequence of crystal protein gene isolated from *B. thuringiensis* subspecies entomocidus . . . ," Nucleic Acids Research (1988), p. 6240, vol. 16, Issue 13.
Sanchis et al., "Nucleotide sequence and analysis of the N-terminal coding region of the Spodoptera-active . . . ," Molecular Microbiology, 1989, pp. 229-238, vol. 3, Issue 2.

* cited by examiner

*Primary Examiner*—Chih-Min Kam
(74) *Attorney, Agent, or Firm*—Baker & Daniels LLP

(57) ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

8 Claims, 1 Drawing Sheet

A. *Bacillus thuringiensis* HD-1
B. *Bacillus thuringiensis* PS81I

BACILLUS THURINGIENSIS ISOLATE ACTIVE AGAINST LEPIDOPTERAN PESTS, AND GENES ENCODING NOVEL LEPIDOPTERAN-ACTIVE TOXINS

CROSS-REFERENCE TO RELATED APPLICATIONS

This is a divisional of application Ser. No. 10/825,751, filed Apr. 16, 2004, now U. S. Pat. No. 7,138,568; which is a divisional of application Ser. No. 09/837,961, filed Apr. 19, 2001, now U.S. Pat. No. 6,737,273; which is a divisional of application Ser. No. 09/521,344, filed Mar. 9, 2000, now U.S. Pat. No. 6,573,240; which is a divisional of application Ser. No. 08/933,891, filed Sep. 19, 1997, now U.S. Pat. No. 6,096,708; which is a continuation of application Ser. No. 08/356,034, filed Dec. 14, 1994, now U.S. Pat. No. 5,691,308; which is a continuation of Ser. No. 08/210,110, filed Mar. 17, 1994, now abandoned; which is a continuation of Ser. No. 07/865,168, filed Apr. 9, 1992, now abandoned; which is a division of Ser. No. 07/451,261, filed Dec. 14, 1989, now U.S. Pat. No. 5,188,960; which is a continuation-in-part of Ser. No. 07/371,955, filed Jun. 27, 1989, now U.S. Pat. No. 5,126,133.

BACKGROUND OF THE INVENTION

The most widely used microbial pesticides are derived from the bacterium *Bacillus thuringiensis*. This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. kurstaki HD-1 produces a crystal inclusion consisting of a biotoxin called a delta toxin which is toxic to the larvae of a number of lepidopteran insects. The cloning, sequencing, and expression of this B.t. crystal protein gene in *Escherichia coli* has been described in the published literature (Schnepf, H. E. and Whitely, H. R. [1981] Proc. Natl. Acad. Sci. USA 78:2893-2897; Schnepf et al.). U.S. Pat. No. 4,448,885 and U.S. Pat. No. 4,467,036 both disclose the expression of B.t. crystal protein in *E. coli*.

BRIEF SUMMARY OF THE INVENTION

The subject invention concerns a novel *Bacillus thuringiensis* isolate designated B.t. PS81I which has activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises the novel B.t. isolate denoted B.t. PS81I, mutants thereof, and novel δ-endotoxin genes derived from this B.t. isolate which encode proteins which are active against lepidopteran pests.

BRIEF DESCRIPTION OF THE SEQUENCES

SEQ ID NO:1 is the nucleotide sequence of the novel B.t. toxin gene PS81IA2.

SEQ ID NO:2 is the amino acid sequence of the novel B.t. toxin PS81IA2.

SEQ ID NO:3 is the nucleotide sequence of the novel B.t. toxin gene PS81IB.

SEQ ID NO:4 is the amino acid sequence of the novel B.t. toxin PS81IB.

SEQ ID NO:5 is the nucleotide sequence of the novel B.t. toxin gene PS81IB2.

SEQ ID NO:6 is the amino acid sequence of the novel B.t. toxin PS81IB2.

SEQ ID NO:7 is the nucleotide sequence of the novel B.t. toxin gene PS81IA.

SEQ ID NO:8 is the amino acid sequence of the novel B.t. toxin PS81IA.

SEQ ID NO:9 is the 42-mer oligonucleotide constructed to the sequence of the insert in pM2,31-4.

SEQ ID NO:10 is the 40-mer oligonucleotide constructed to the sequence of the insert in pM2,31-1.

BRIEF DESCRIPTION OF THE DRAWINGS

FIG. 1—agarose gel electrophoresis of plasmid preparations from B.t. HD-1 and B.t. PS81I.

DETAILED DISCLOSURE OF THE INVENTION

The novel toxin genes of the subject invention were obtained from a novel lepidopteran-active *B. thuringiensis* (B.t.) isolate designated PS81I.

Characteristics of B.t. PS81I

Colony morphology—Large colony, dull surface, typical B.t.

Vegetative cell morphology—typical B.t.

Flagellar serotype—7, aizawai.

Intracellular inclusions—sporulating cells produce a bipyramidal crystal.

Plasmid preparations—agarose gel electrophoresis of plasmid preparations distinguishing B.t. PS81I from B.t. HD-1. See FIG. 1.

Alkali-soluble proteins—SDS-PAGE analysis shows a protein band at ca. 130,000 daltons.

Unique toxins—four unique toxins have been identified in B.t. PS81I.

Activity—B.t. PS81I kills all Lepidoptera tested.

Bioassay procedures:

B.t. PS81I spores and crystals were tested against: Beet Armyworm, *Spodoptera exigua*; Diamondback Moth, *Plutella xylostella*; Western Spruce Budworm, *Choristoneura occidentalis*.

LC50 values were as follows:

Beet Armyworm—2.53 ppm

Diamondback Moth—0.16 ppm

Western Spruce Budworm—3.2 ppm

Bioassay procedure: dilutions are prepared of a spore and crystal pellet, mixed with USDA Insect Diet (Technical Bulletin 1528, U.S. Department of Agriculture), and poured into small plastic trays. Larvae are placed on the diet mixture and held at 25° C. (late 2nd instar Diamondback Moth larvae, early 2nd instar Beet Armyworm larvae, 4th instar Western Spruce Budworm larvae). Mortality is recorded after six days.

*B. thuringiensis* PS81I, NRRL B-18484, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against *Lepidoptera*, e.g., caterpillars. B.t. PS81I, and mutants thereof, can be used to control lepidopteran pests.

A subculture of B.t. PS81I and the *E. coli* hosts harboring the toxin genes of the invention, were deposited in the permanent collection of the Northern Research Laboratory, U.S. Department of Agriculture, Peoria, Ill., USA. The accession numbers and deposit dates are as follows:

| Subculture | Accession Number | Deposit Date |
| --- | --- | --- |
| B.t. PS81I | NRRL B-18484 | Apr. 19, 1989 |
| *E. coli* (NM522)(pMYC392) | NRRL B-18498 | May 17, 1989 |
| *E. coli* (NM522)(pMYC393) | NRRL B-18499 | May 17, 1989 |
| *E. coli* (NM522)(pMYC394) | NRRL B-18500 | May 17, 1989 |
| *E. coli* (NM522)(pMYC1603) | NRRL B-18517 | Jun. 30, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin genes of the subject invention can be introduced into a wide variety of microbial hosts. Expression of the toxin gene results, directly or indirectly, in the intracellular production and maintenance of the pesticide. With suitable hosts, e.g., *Pseudomonas,* the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc,* and *Alcaligenes;* fungi, particularly yeast, e.g., genera *Saccharomyces, Cryptococcus, Kluyveromyces, Sporobolomyces, Rhodotorula,* and *Aureobasidium.* Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the ip gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as *Escherichia, Erwinia, Shigella, Salmonella,* and *Proteus;* Bacillaceae; Rhizobiceae, such as *Rhizobium;* Spirillaceae, such as photobacterium, *Zymomonas, Serratia, Aeromonas, Vibrio, Desulfovibrio, Spirillum;* Lactobacillaceae; *Pseudomonadaceae,* such as *Pseudomonas* and *Acetobacter;* Azotobacteraceae, Actinomycetales, and Nitrobacteraceae. Among eukaryotes are fungi, such as Phycomycetes and Ascomycetes, which includes yeast, such as *Saccharomyces* and *Schizosaccharomyces;* and Basidiomycetes yeast, such as *Rhodotorula, Aureobasidium, Sporobolomyces,* and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* sp., *Aureobasidium* sp., *Saccharomyces* sp., and *Sporobolomyces* sp.; phylloplane organisms such as *Pseudomonas* sp., *Erwinia* sp. and *Flavobacterium* sp.; or such other organisms as *Escherichia, Lactobacillus* sp., *Bacillus* sp., *Streptomyces* sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81I can be made by procedures well known in the art. For example, an asporogenous mutant can be obtained through ethylmethane sulfonate (EMS) mutagenesis of PS81I. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. PS81I

A subculture of B.t. PS81I, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g | pH 7.2

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Genes From Isolate PS81I and Transformation into *Escherichia Coli*

Total cellular DNA was prepared from B.t. cells grown to a low optical density ($OD_{600}$=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81I and B.t.k. HD-1 was digested with EcoRI and separated by electrophoresis on a 0.8% (w/v) Agarose-TAE (50 mM Tris-Cl, 20 mM NaOAc, 2.5 mM EDTA, pH=8.0) buffered gel. A Southern blot of the gel was hybridized with a [$^{32}$P] radiolabeled probe against the 3.2 Kb NsiI to NsiI fragment of the toxin gene contained in plasmid pM3,130-7 of NRRL B-18332 and the 2.4 Kb NsiI to KpnI fragment of the "4.5 Kb class" toxin gene (Kronstad and Whitely [1986] Gene USA 43:29-40). These two fragments were combined and used as the probe. Results show that hybridizing fragments of PS81I are distinct from those of HD-1. Specifically, in the 1.5 Kb to 2.5 Kb size range, 2.3 Kb, 1.95 Kb, and 1.6 Kb hybridizing bands were detected in PS81I instead of the single 1.9 Kb hybridizing band in HD-1.

The following description outlines the steps taken in cloning two of the three EcoRI fragments described above. Two hundred micrograms of PS81I total cellular DNA was digested with EcoRI and separated by electrophoresis on a preparative 0.8% (w/v) Agarose-TAE gel. The 1.5 Kb to 2.3 Kb region of the gel was cut out and the DNA from it was electroeluted and concentrated using an ELUTIP™-d (Schleicher and Schuell, Keene, N.H.) ion exchange column according to the manufacturer's specification. The isolated EcoRI fragments were ligated to LAMBDA ZAP™ EcoRI arms (Stratagene Cloning Systems, La Jolla, Calif.) and packaged using Gigapak GOLD™ (Stratagene) extracts. The packaged recombinant phage were plated with *E. coli* strain BB4 (Stratagene) to give high plaque density. The plaques were screened by standard nucleic acid hybridization procedures with radiolabeled probe. The plaques that hybridized were purified and re-screened at a lower plaque density. The resulting purified phage were grown with R408 M13 helper phage (Stratagene) and the recombinant BlueScript™ (Stratagene) plasmid was automatically excised and packaged. The "phagemid" was re-infected in XLI-Blue *E. coli* cells (Stratagene) as part of the automatic excision process. The infected XLI-Blue cells were screened for ampicillin resistance and the resulting colonies were analyzed by a standard rapid plasmid purification procedure to identify the desired plasmids. The plasmids, designated pM2,31-4 and pM2,31-1, contain approximately 1.95 Kb and 1.6 Kb EcoRI inserts, respectively. The DNA sequence of both inserts was determined using Stratagene's T7 and T3 oligonucleotide primers plus a set of existing internal B.t. endotoxin gene oligonucleotide primers. About 500 bp of the insert in pM2,31-4 was sequenced. In the same manner, approximately 1.0 Kb of the insert in pM2,31-1 was sequenced. Data analysis comparing the two sequences to other cloned and sequenced B.t. endotoxin genes showed that two distinct, unique partial toxin gene sequences had been found. Synthetic oligonucleotides were constructed to regions in both sequences that had minimum homology to other characterized B.t. endotoxin genes. The 42-mer oligonucleotide constructed to the sequence of the insert in pM2,31-4 was GGATACCGGTGACCCATTAACATTCCAATCTTTTAGTTACGC (SEQ ID NO:9); it was used to isolate a toxin gene sequence called 81IA. The 40-mer oligonucleotide constructed to the sequence of the insert in pM2,31-1 was GAAGTTTATGGCCTCTTTCTGTAGAAAATCAAATTGGACC (SEQ ID NO:10); it was used to isolate a toxin gene sequence called 81IB.

In order to clone both complete toxin genes, a Sau3A partial library was constructed. PS81I total cellular DNA partially digested with Sau3A and size fractionated by electrophoresis into a mixture of 9-23 Kb fragments on a 0.6% agarose-TAE gel, and purified as described previously, was ligated into LambdaGEM-11™ (PROMEGA). The packaged phage were plated on P2392 *E. coli* cells (Stratagene) at a high titer and screened using the radiolabeled synthetic oligonucleotides (aforementioned) as nucleic acid hybridization probes. Hybridizing plaques, using each probe, were rescreened at a lower plaque density. Purified plaques that hybridized with either probe were used to infect P2392 *E. coli* cells in liquid culture for preparation of phage for DNA isolation. DNA was isolated by standard procedures. Preparative amounts of DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pUC19 (NEB). The ligation mix was introduced by transformation into DH5(α) competent *E. coli* cells (BRL) and plated on LB agar containing ampicillin, isopropyl-(β)-D-thiogalactoside (IPTG), and 5-bromo-4-chloro-3-indolyl-(β)-D-galactoside (XGAL). White colonies, with prospective insertions in the (β)-galactosidase gene of pUC19, were subjected to standard rapid plasmid purification procedures to isolate the desired plasmids. Plasmid pM3,122-1 contains a 15 Kb Sau3A fragment isolated using the 81IA oligonucleotide probe. Plasmid pM4,59-1 contains an 18 Kb Sau3A fragment isolated using the 81IB oligonucleotide probe.

Plasmid pM3,122-1 was digested with several restriction enzymes and Southern blotted. The blot was probed with the [$^{32}$P] radiolabeled 81IA specific oligonucleotide probe, as well as the labeled oligonucleotide sequencing primers made to known B.t.k. toxin genes. The resulting autoradiogram showed that two toxin genes were present in tandem on this cloned Sau3A fragment. Plasmid pM3,122-1 had a 4.0 Kb NdeI fragment that hybridized with oligonucleotide probes made to known B.t.k. genes. This fragment, however, did not hybridize with the specific oligonucleotides to 81IA or 81IB; a new toxin gene had been discovered and subsequently was called 81IA2. The 4.0 Kb NdeI fragment was isolated and cloned in pUC19, yielding plasmid pMYC392. The 81IA toxin gene was isolated by digesting pM3,122-1 with HindIII, with resulting deletion of most of the 81IA2 toxin gene. The fragment was recircularized to form pMYC1603. The 81IA toxin gene is unique based on its restriction map and its DNA sequence.

Plasmid pM4,59-1 was digested with several restriction enzymes and Southern blotted. The blot was probed with the [$^{32}$P] radiolabeled 81IB specific oligonucleotide probe, as well as with labeled oligonucleotide sequencing primers made to known B.t.k. toxin genes. The plasmid pM4,59-1 was mapped and found to contain only a partial 81IB toxin gene. The full open reading frame (ORF) of a second toxin gene was discovered on the 18 Kb fragment and called 81IB2. The 81IB2 toxin gene was cloned separately from the 81IB toxin gene by digestion of pM4,59-1 with NdeI and SmaI, filling in the NdeI overhang and ligating the linear fragment back together. The resulting plasmid was called pMYC394. The full ORF of the 81IB toxin gene was isolated from another Sau3A fragment, cloned from the lambda library, on a 7.3 Kb HindIII fragment in pBluescript (Stratagene). The resulting plasmid is pMYC393.

The toxin genes were sequenced by the standard Sanger dideoxy chain termination method using oligonucleotide primers made to the "4.5 Kb class" toxin gene and by "walking" with primers made to the sequences of the new toxin genes. Sequence analysis of the four toxin genes has elucidated unique open reading frames and has deduced unique endotoxin proteins. The following table summarizes the size of each ORF in base pairs and the deduced endotoxin molecular weight in daltons.

| TOXIN GENE | ORF (bp) | DEDUCED MW (daltons) | SEQUENCES |
|---|---|---|---|
| 81IA2 | 3537 | 133,367 | SEQ ID NOs: 1-2 |
| 81IB | 3495 | 132,480 | SEQ ID NOs: 3-4 |
| 81IB2 | 3567 | 134,714 | SEQ ID NOs: 5-6 |
| 81IA | 3716 | 133,621 | SEQ ID NOs: 7-8 |

Endotoxin proteins have been expressed in *Pseudomonas* and/or *Bacillus* from the toxin genes. SDS-PAGE/Western blot analysis, using polyclonal antibodies directed against the "6.6 Kb" class toxin, verified that each gene encodes an immunoreactive protein of approximately 130,000 daltons. The toxin proteins encoded by the genes of the subject invention expressed in either a *Bacillus* or *Pseudomonas* host have activity against all lepidopteran insects tested: *Trichoplusia ni, Spodoptera exigua, Plutella xylostella*, and *Choristoneura occidentalis*.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., New England Biolabs, Beverly, Mass., or Boehringer-Mannheim, Indianapolis, Ind. The enzymes are used according to the instructions provided by the supplier.

The plasmids containing the B.t. toxin genes can be removed from the transformed host microbes by use of standard well-known procedures. For example, the host microbes can be subjected to cleared lysate isopycnic density gradient procedures, and the like, to recover the desired plasmid.

EXAMPLE 3

Insertion of Toxin Genes Into Plants

The novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *B. thuringiensis* Genes Into Baculoviruses

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al. (Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequences encoding the novel B.t. toxin genes are shown in SEQ ID NO:1, SEQ ID NO:3, SEQ ID NO:5, and SEQ ID NO:7. The deduced amino acid sequences are shown in SEQ ID NO:2, SEQ ID NO:4, SEQ ID NO:6, and SEQ ID NO:8.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | |
|---|---|
| Phenylalanine (Phe) | TTK |
| Leucine (Leu) | XTY |
| Isoleucine (Ile) | ATM |
| Methionine (Met) | ATG |
| Valine (Val) | GTL |
| Serine (Ser) | QRS |

-continued

| | |
|---|---|
| Proline (Pro) | CCL |
| Threonine (Thr) | ACL |
| Alanine (Ala) | GCL |
| Tyrosine (Tyr) | TAK |
| Termination signal | TAJ |
| Histidine (His) | CAK |
| Glutamine (Gln) | CAJ |
| Asparagine (Asn) | AAK |
| Lysine (Lys) | AAJ |
| Aspartic acid (Asp) | GAK |
| Glutamic acid (Glu) | GAJ |
| Cysteine (Cys) | TGK |
| Tryptophan (Trp) | TGG |
| Arginine (Arg) | WGZ |
| Glycine (Gly) | GGL |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequences of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is retained to some degree.

The invention claimed is:

1. A recombinant DNA transfer vector comprising a polynucleotide sequence that encodes a toxin comprising an insecticidal fragment of the amino acid sequence SEQ ID NO: 4.

2. The vector of claim 1 wherein said polynucleotide sequence comprises a fragment of the nucleotide sequence of SEQ ID NO:3 that is sufficient to encode an insecticidal toxin.

3. The vector of claim 2 wherein said vector is transferred to and replicated in a prokaryotic or eukaryotic host cell.

4. The vector of claim 1 wherein said vector is transferred to and replicated in a prokaryotic or eukaryotic host cell.

5. An isolated polynucleotide that encodes a *Bacillus thuringiensis* toxin comprising an insecticidal fragment of a protein comprising the amino acid sequence SEQ ID NO:4.

6. The isolated polynucleotide according to claim 5 wherein said polynucleotide comprises a fragment of the nucleotide sequence of SEQ ID NO:3.

7. A recombinant microbial or plant cell comprising the isolated polynucleotide sequence of claim 5.

8. The recombinant microbial or plant cell according to claim 7 wherein said polynucleotide comprises a fragment of the nucleotide sequence of SEQ ID NO:3.

* * * * *

SEQUENCE LISTING

<160> NUMBER OF SEQ ID NOS: 10

<210> SEQ ID NO 1
<211> LENGTH: 3528
<212> TYPE: DNA
<213> ORGANISM: Bacillus thuringiensis

<400> SEQUENCE: 1

```
atgaataatc agaatcaatg cgttccttat aactgtttga atgatccgac aattgaaata      60
ttagaaggag aaagaataga aactggttac accccaatag atatttcctt gtcgctaacg     120
caatttctgt tgagtgaatt tgtcccaggt gctgggtttg tattaggttt aattgattta     180
atatgggggt ttgtgggtcc ctctcaatgg gatgcatttc ttgtgcaaat gaacagtta      240 attaaccaaa gaatagagga attcgctagg aaccaagcaa tttctagatt agaagggcta     300
agcaaccttt atcaaattta cgcagaagct tttagagagt gggaagcaga tcctactaat     360
ccagcattaa cagaagagat gcgtattcag ttcaatgaca tgaacagtgc tcttacaacc     420
gctattcctc tttttacagt tcaaaattat caagtacctc ttctatcagt atatgttcaa     480
gctgcaaatt tacatttatc ggttttgaga gatgtttcag tgtttggaca acgttgggga     540
tttgatgtag caacaatcaa tagtcgttat aatgatttaa ctaggcttat tggcacctat     600
acagattatg ctgtacgctg gtataatacg ggattagaac gtgtatgggg accggattct     660
agagattggg taaggtataa tcaatttaga agagagctaa cactaactgt attagatatc     720
gtttctctgt tcccgaacta tgatagtaga acgtatccaa ttcgaacagt ttcccaatta     780
actagagaaa tttatacaaa cccagtatta gaaaattttg atggtagttt tcgtggaatg     840 gctcagaaa tagaacagaa tattaggcaa ccacatctta tggatctcct taatagtata     900
accatttata ctgatgtgca tagaggcttt aattattggt caggacatca aataacagct     960
```

```
tctcctgtcg gttttgcggg gccagaattt acttttccta gatatggaac catgggaaat   1020
gctgctccac ccgtactgat ctcaactact ggtttgggga ttttagaac attatcttca    1080 cctctttaca gaagaattat acttggttca ggcccaaata atcagaacct gtttgtcctt   1140
gatggaacgg aatttcttt tgcctcccta acagccgatt taccttctac tatatacaga    1200
caaaggggaa cggtcgattc actagatgta ataccgccac aggataatag tgtgccagca   1260
cgtgcgggat ttagtcatcg attaagtcat gttacaatgc tgagccaagc agctggagca   1320
gtttacacct tgagagctcc aacgttttct tggcgacatc gtagtgctga attctctaac   1380
ctaattcctt catcacaaat cacacagata cctttaacaa agtctattaa tcttggctct   1440
gggacctctg ttgttaaagg accaggattt acaggaggag atattcttcg aataacttca   1500
cctggccaga tttcaacctt aagagtgact attacggcac cattatcaca aagatatcgc   1560
gtaagaattc gctacgcttc tactacaaat ttacaattcc atacatcaat tgacggaaga   1620
cctattaatc aggggaattt ttcagcaact atgagtagtg ggggtaattt acagtccgga   1680
agctttagga ctgcaggttt tactactccg tttaactttt caaatggatc aagtatattt   1740
acgttaagtg ctcatgtctt caattcaggc aatgaagttt atatagagcg aattgaattt   1800
gttccggcag aagtaacatt tgaggcgaaa tatgatttag aaagagcgca agaggcggtg   1860
aatgctctgt ttacttcttc caatcaacta ggattaaaaa caaatgtgac ggactatcat   1920
attgatcaag tgtccaatct agtcgaatgt ttatccggtg aattctgtct ggatgaaaag   1980
agagaattgt ccgagaaagt caaacatgcg aaccgactca gtgatgagcg aatttactt    2040 caagacccaa acttcagagg catcaataga caaccagacc gtggctggag aggcagtacg   2100
gatattacca tccaaggagg agatgacgta ttcaaagaga attacgtcac actaccgggt   2160 accttaatg agtgttatcc tacgtatctg tatcaaaaaa tagatgagtc gaaattaaaa    2220
gcctataccc gttaccaatt aagagggtac atcgaggata gtcaacactt agaaatctat   2280
ttaattcgct acaatacaaa acacgaaaca gtaaatgtgc caggtacggg ttccttatgg   2340
ccgctttcag tcgaaaatcc aattggaaag tgcggagaac caaatcgatg cgcaccacaa   2400
cttgaatgga atcctgatct agattgttcc tgcagagacg gggaaaaatg tgcacatcac   2460
tcccatcatt tctccttgga cattgatatt ggatgtacag atttaaatga aacttaggt    2520 gtatgggtga tattcaaaat taagatgcaa gatggtcacg caagactagg taatctagag   2580
tttctcgaag agaaaccatt agtaggcgaa tcgttagcac gcgtgaagag agcggagaag   2640
aagtggagag acaaacgaga gaaattgcaa gtggaaacaa atatcgttta taagaggca    2700 aaagaatctg tagatgcttt atttgtgaac tctcaatatg atagattaca agcggatacc   2760
gacatcgcga tgattcatgc ggcagataaa cgcgttcatc gaattcgaga agcatatctt   2820
ccagagttat ctgtaattcc gggtgtcaat gcgggcattt ttgaagaatt agagggacgt   2880
attttcacag cctactcttt atatgatgcg agaaatgtca ttaaaaatgg cgatttcaat   2940
aatggcttat catgctggaa cgtgaaaggg catgtagatg tagaagaaca aaacaaccac   3000
cgttcggttc ttgttgtccc ggaatgggaa gcagaggtgt cacaagaggt tcgtgtctgt   3060
ccaggtcgtg gctatatcct acgtgttaca gcgtacaaag agggatatgg agaaggttgc   3120
gtaacgattc atgagatcga agacaataca gacgaactga aattcagcaa ctgtgtagaa   3180
gaggaagtat atccaaacaa cacggtaacg tgtaatgatt atactgcaaa tcaagaagaa   3240 tacggggggtg cgtacacttc tcgtaatcgt ggatatggtg aatcttatga aagtaattct   3300
```

```
tccataccag ctgagtatgc gccagtttat gaggaagcat atatagatgg aagaaaagag    3360
aatccttgtg aatctaacag aggatatggg gattacacgc cactaccagc tggttatgtg    3420
acaaaagaat tagagtactt cccagaaacc gataaggtat ggattgagat cggggaaacg    3480
gaaggaacat tcatcgtgga tagcgtggaa ttactcctta tggaggaa                 3528
```

<210> SEQ ID NO 2
<211> LENGTH: 1176
<212> TYPE: PRT
<213> ORGANISM: Bacillus thuringiensis

<400> SEQUENCE: 2

```
Met Asn Asn Gln Asn Gln Cys Val Pro Tyr Asn Cys Leu Asn Asp Pro
 1               5                  10                  15

Thr Ile Glu Ile Leu Glu Gly Glu Arg Ile Glu Thr Gly Tyr Thr Pro
            20                  25                  30

Ile Asp Ile Ser Leu Ser Leu Thr Gln Phe Leu Leu Ser Glu Phe Val
        35                  40                  45

Pro Gly Ala Gly Phe Val Leu Gly Leu Ile Asp Leu Ile Trp Gly Phe
    50                  55                  60

Val Gly Pro Ser Gln Trp Asp Ala Phe Leu Val Gln Ile Glu Gln Leu
65                  70                  75                  80

Ile Asn Gln Arg Ile Glu Glu Phe Ala Arg Asn Gln Ala Ile Ser Arg
                85                  90                  95

Leu Glu Gly Leu Ser Asn Leu Tyr Gln Ile Tyr Ala Glu Ala Phe Arg
            100                 105                 110

Glu Trp Glu Ala Asp Pro Thr Asn Pro Ala Leu Thr Glu Glu Met Arg
        115                 120                 125

Ile Gln Phe Asn Asp Met Asn Ser Ala Leu Thr Thr Ala Ile Pro Leu
    130                 135                 140

Phe Thr Val Gln Asn Tyr Gln Val Pro Leu Leu Ser Val Tyr Val Gln
145                 150                 155                 160

Ala Ala Asn Leu His Leu Ser Val Leu Arg Asp Val Ser Val Phe Gly
                165                 170                 175

Gln Arg Trp Gly Phe Asp Val Ala Thr Ile Asn Ser Arg Tyr Asn Asp
            180                 185                 190

Leu Thr Arg Leu Ile Gly Thr Tyr Thr Asp Tyr Ala Val Arg Trp Tyr
        195                 200                 205

Asn Thr Gly Leu Glu Arg Val Trp Gly Pro Asp Ser Arg Asp Trp Val
    210                 215                 220

Arg Tyr Asn Gln Phe Arg Arg Glu Leu Thr Leu Thr Val Leu Asp Ile
225                 230                 235                 240

Val Ser Leu Phe Pro Asn Tyr Asp Ser Arg Thr Tyr Pro Ile Arg Thr
                245                 250                 255

Val Ser Gln Leu Thr Arg Glu Ile Tyr Thr Asn Pro Val Leu Glu Asn
            260                 265                 270

Phe Asp Gly Ser Phe Arg Gly Met Ala Gln Arg Ile Glu Gln Asn Ile
        275                 280                 285

Arg Gln Pro His Leu Met Asp Leu Leu Asn Ser Ile Thr Ile Tyr Thr
    290                 295                 300

Asp Val His Arg Gly Phe Asn Tyr Trp Ser Gly His Gln Ile Thr Ala
305                 310                 315                 320

Ser Pro Val Gly Phe Ala Gly Pro Glu Phe Thr Phe Pro Arg Tyr Gly
                325                 330                 335
```

-continued

```
Thr Met Gly Asn Ala Ala Pro Pro Val Leu Ile Ser Thr Thr Gly Leu
            340                 345                 350

Gly Ile Phe Arg Thr Leu Ser Ser Pro Leu Tyr Arg Ile Ile Leu
        355                 360                 365

Gly Ser Gly Pro Asn Asn Gln Asn Leu Phe Val Leu Asp Gly Thr Glu
        370                 375                 380

Phe Ser Phe Ala Ser Leu Thr Ala Asp Leu Pro Ser Thr Ile Tyr Arg
385                 390                 395                 400

Gln Arg Gly Thr Val Asp Ser Leu Asp Val Ile Pro Pro Gln Asp Asn
                405                 410                 415

Ser Val Pro Ala Arg Ala Gly Phe Ser His Arg Leu Ser His Val Thr
                420                 425                 430

Met Leu Ser Gln Ala Ala Gly Ala Val Tyr Thr Leu Arg Ala Pro Thr
        435                 440                 445

Phe Ser Trp Arg His Arg Ser Ala Glu Phe Ser Asn Leu Ile Pro Ser
    450                 455                 460

Ser Gln Ile Thr Gln Ile Pro Leu Thr Lys Ser Ile Asn Leu Gly Ser
465                 470                 475                 480

Gly Thr Ser Val Val Lys Gly Pro Gly Phe Thr Gly Asp Ile Leu
                485                 490                 495

Arg Ile Thr Ser Pro Gly Gln Ile Ser Thr Leu Arg Val Thr Ile Thr
            500                 505                 510

Ala Pro Leu Ser Gln Arg Tyr Arg Val Arg Ile Arg Tyr Ala Ser Thr
        515                 520                 525

Thr Asn Leu Gln Phe His Thr Ser Ile Asp Gly Arg Pro Ile Asn Gln
        530                 535                 540

Gly Asn Phe Ser Ala Thr Met Ser Ser Gly Gly Asn Leu Gln Ser Gly
545                 550                 555                 560

Ser Phe Arg Thr Ala Gly Phe Thr Thr Pro Phe Asn Phe Ser Asn Gly
                565                 570                 575

Ser Ser Ile Phe Thr Leu Ser Ala His Val Phe Asn Ser Gly Asn Glu
            580                 585                 590

Val Tyr Ile Glu Arg Ile Glu Phe Val Pro Ala Glu Val Thr Phe Glu
        595                 600                 605

Ala Glu Tyr Asp Leu Glu Arg Ala Gln Glu Ala Val Asn Ala Leu Phe
    610                 615                 620

Thr Ser Ser Asn Gln Leu Gly Leu Lys Thr Asn Val Thr Asp Tyr His
625                 630                 635                 640

Ile Asp Gln Val Ser Asn Leu Val Glu Cys Leu Ser Gly Glu Phe Cys
                645                 650                 655

Leu Asp Glu Lys Arg Glu Leu Ser Glu Lys Val Lys His Ala Asn Arg
                660                 665                 670

Leu Ser Asp Glu Arg Asn Leu Leu Gln Asp Pro Asn Phe Arg Gly Ile
        675                 680                 685

Asn Arg Gln Pro Asp Arg Gly Trp Arg Gly Ser Thr Asp Ile Thr Ile
    690                 695                 700

Gln Gly Gly Asp Asp Val Phe Lys Glu Asn Tyr Val Thr Leu Pro Gly
705                 710                 715                 720

Thr Phe Asn Glu Cys Tyr Pro Thr Tyr Leu Tyr Gln Lys Ile Asp Glu
                725                 730                 735

Ser Lys Leu Lys Ala Tyr Thr Arg Tyr Gln Leu Arg Gly Tyr Ile Glu
                740                 745                 750

Asp Ser Gln His Leu Glu Ile Tyr Leu Ile Arg Tyr Asn Thr Lys His
```

-continued

```
            755                 760                 765
Glu Thr Val Asn Val Pro Gly Thr Gly Ser Leu Trp Pro Leu Ser Val
770                 775                 780

Glu Asn Pro Ile Gly Lys Cys Gly Pro Asn Arg Cys Ala Pro Gln
785                 790                 795                 800

Leu Glu Trp Asn Pro Asp Leu Asp Cys Ser Cys Arg Asp Gly Glu Lys
                805                 810                 815

Cys Ala His His Ser His His Phe Ser Leu Asp Ile Asp Ile Gly Cys
                    820                 825                 830

Thr Asp Leu Asn Glu Asn Leu Gly Val Trp Val Ile Phe Lys Ile Lys
                    835                 840                 845

Met Gln Asp Gly His Ala Arg Leu Gly Asn Leu Glu Phe Leu Glu Glu
850                 855                 860

Lys Pro Leu Val Gly Glu Ser Leu Ala Arg Val Lys Arg Ala Glu Lys
865                 870                 875                 880

Lys Trp Arg Asp Lys Arg Glu Lys Leu Gln Val Glu Thr Asn Ile Val
                    885                 890                 895

Tyr Lys Glu Ala Lys Glu Ser Val Asp Ala Leu Phe Val Asn Ser Gln
                900                 905                 910

Tyr Asp Arg Leu Gln Ala Asp Thr Asp Ile Ala Met Ile His Ala Ala
                915                 920                 925

Asp Lys Arg Val His Arg Ile Arg Glu Ala Tyr Leu Pro Glu Leu Ser
930                 935                 940

Val Ile Pro Gly Val Asn Ala Gly Ile Phe Glu Glu Leu Glu Gly Arg
945                 950                 955                 960

Ile Phe Thr Ala Tyr Ser Leu Tyr Asp Ala Arg Asn Val Ile Lys Asn
                    965                 970                 975

Gly Asp Phe Asn Asn Gly Leu Ser Cys Trp Asn Val Lys Gly His Val
                980                 985                 990

Asp Val Glu Glu Gln Asn Asn His Arg Ser Val Leu Val Val Pro Glu
                995                 1000                1005

Trp Glu Ala Glu Val Ser Gln Glu Val Arg Val Cys Pro Gly Arg
    1010                1015                1020

Gly Tyr Ile Leu Arg Val Thr Ala Tyr Lys Glu Gly Tyr Gly Glu
    1025                1030                1035

Gly Cys Val Thr Ile His Glu Ile Glu Asp Asn Thr Asp Glu Leu
    1040                1045                1050

Lys Phe Ser Asn Cys Val Glu Glu Val Tyr Pro Asn Asn Thr
    1055                1060                1065

Val Thr Cys Asn Asp Tyr Thr Ala Asn Gln Glu Glu Tyr Gly Gly
    1070                1075                1080

Ala Tyr Thr Ser Arg Asn Arg Gly Tyr Gly Glu Ser Tyr Glu Ser
    1085                1090                1095

Asn Ser Ser Ile Pro Ala Glu Tyr Ala Pro Val Tyr Glu Glu Ala
    1100                1105                1110

Tyr Ile Asp Gly Arg Lys Glu Asn Pro Cys Glu Ser Asn Arg Gly
    1115                1120                1125

Tyr Gly Asp Tyr Thr Pro Leu Pro Ala Gly Tyr Val Thr Lys Glu
    1130                1135                1140

Leu Glu Tyr Phe Pro Glu Thr Asp Lys Val Trp Ile Glu Ile Gly
    1145                1150                1155

Glu Thr Glu Gly Thr Phe Ile Val Asp Ser Val Glu Leu Leu Leu
    1160                1165                1170
```

Met Glu Glu
1175

<210> SEQ ID NO 3
<211> LENGTH: 3495
<212> TYPE: DNA
<213> ORGANISM: Bacillus thuringiensis

<400> SEQUENCE: 3

| | | | | | |
|---|---|---|---|---|---|
| atggaaataa | ataatcaaaa | ccaatgtgtg | ccttacaatt | gtttaagtaa | tcctaaggag | 60 |
| ataatattag | gcgaggaaag | gctagaaaca | gggaatactg | tagcagacat | tcattaggg | 120 |
| cttattaatt | ttctatattc | taattttgta | ccaggaggag | gatttatagt | aggtttacta | 180 |
| gaattaatat | ggggatttat | agggccttcg | caatgggata | ttttttttagc | tcaaattgag | 240 |
| caattgatta | gtcaaagaat | agaagaattt | gctaggaatc | aggcaatttc | aagattggag | 300 |
| gggctaagca | atctttataa | ggtctatgtt | agagcgttta | gcgactggga | gaaagatcct | 360 |
| actaatcctg | ctttaaggga | gaaatgcgt | atacaattta | tgacatgaa | tagtgctctc | 420 |
| ataacggcta | ttccactttt | tagagttcaa | aattatgaag | ttgctctttt | atctgtatat | 480 |
| gttcaagccg | caaacttaca | tttatctatt | ttaagggatg | tttcagtttt | cggagaaaga | 540 |
| tggggatatg | atacagcgac | tatcaataat | cgctatagtg | atctgactag | ccttattcat | 600 |
| gtttatacta | accattgtgt | ggatacgtat | aatcagggat | taaggcgttt | ggaaggtcgt | 660 |
| tttcttagcg | attggattgt | atataatcgt | ttccggagac | aattgacaat | tcagtatta | 720 |
| gatattgttg | cgttttttcc | aaattatgat | attagaacat | atccaattca | aacagctact | 780 |
| cagctaacga | gggaagtcta | tctggattta | cctttttatta | atgaaaatct | ttctcctgca | 840 |
| gcaagctatc | caacctttc | agctgctgaa | agtgctataa | ttagaagtcc | tcatttagta | 900 |
| gacttttttaa | atagctttac | catttataca | gatagtctgg | cacgttatgc | atattgggga | 960 |
| gggcacttgg | taaattcttt | ccgcacagga | accactacta | atttgataag | atccccttta | 1020 |
| tatggaaggg | aaggaaatac | agagcgcccc | gtaactatta | ccgcatcacc | tagcgtacca | 1080 |
| atatttagaa | cactttcata | tattacaggc | cttgacaatt | caaatcctgt | agctggaatc | 1140 |
| gagggagtgg | aattccaaaa | tactataagt | agaagtatct | atcgtaaaag | cggtccaata | 1200 |
| gattctttta | gtgaattacc | acctcaagat | gccagcgtat | ctcctgcaat | tgggtatagt | 1260 |
| caccgtttat | gccatgcaac | atttttagaa | cggattagtg | gaccaagaat | agcaggcacc | 1320 |
| gtattttctt | ggacacaccg | tagtgccagc | cctactaatg | aagtaagtcc | atctagaatt | 1380 |
| acacaaattc | catgggtaaa | ggcgcatact | cttgcatctg | tgcctccgt | cattaaaggt | 1440 |
| cctggattta | caggtggaga | tattctgact | aggaatagta | tgggcgagct | ggggaccta | 1500 |
| cgagtaacct | tcacaggaag | attaccacaa | agttattata | tacgtttccg | ttatgcttcg | 1560 |
| gtagcaaata | ggagtggtac | atttagatat | tcacagccac | cttcgtatgg | aatttcatt | 1620 |
| ccaaaaacta | tggacgcagg | tgaaccacta | acatctcgtt | cgttcgctca | tacaacactc | 1680 |
| ttcactccaa | taacctttc | acgagctcaa | gaagaatttg | atctatacat | ccaatcgggt | 1740 |
| gtttatatag | atcgaattga | atttataccg | gttactgcaa | catttgaggc | agaatatgat | 1800 |
| ttagaaaagag | cgcaaaaggt | ggtgaatgcc | ctgtttacgt | ctacaaacca | actagggcta | 1860 |
| aaaacagatg | tgacggatta | tcatattgat | caggtatcca | atctagttgc | gtgtttatcg | 1920 |
| gatgaatttt | gtctggatga | aaagagagaa | ttgtccgaga | agttaaaca | tgcaaagcga | 1980 |
| ctcagtgatg | agcggaattt | acttcaagat | ccaaacttca | gagggatcaa | taggcaacca | 2040 |

```
gaccgtggct ggagaggaag tacggatatt actatccaag gaggagatga cgtattcaaa    2100
gagaattacg ttacgctacc gggtaccttt gatgagtgct atccaacgta tttatatcaa    2160
aaaatagatg agtcgaaatt aaaagcctat acccgttatc aattaagagg gtatatcgaa    2220
gatagtcaag acttagaaat ctatttaatt cgttacaatg caaaacacga aatagtaaat    2280
gtaccaggta caggaagttt atggcctctt tctgtagaaa atcaaattgg accttgtgga    2340
gaaccgaatc gatgcgcgcc acaccttgaa tggaatcctg atttacactg ttcctgcaga    2400
gacggggaaa aatgtgcaca tcattctcat catttctctt tggacattga tgttggatgt    2460
acagacttaa atgaggactt aggtgtatgg gtgatattca agattaagac gcaagatggc    2520
cacgcacgac tagggaatct agagtttctc gaagagaaac cattattagg agaagcacta    2580
gctcgtgtga aaagagcgga gaaaaatgg agagacaaac gcgaaacatt acaattggaa    2640
acaactatcg tttataaaga ggcaaaagaa tctgtagatg ctttatttgt aaactctcaa    2700
tatgatagat acaagcgga tacgaacatc gcgatgattc atgcggcaga taaacgcgtt    2760
catagaattc gagaagcgta tctgccggag ctgtctgtga ttccgggtgt caatgcggct    2820
atttttgaag aattagaaga gcgtattttc actgcatttt ccctatatga tgcgagaaat    2880
attattaaaa atggcgattt caataatggc ttattatgct ggaacgtgaa agggcatgta    2940
gaggtagaag aacaaaacaa tcaccgttca gtcctggtta tcccagaatg ggaggcagaa    3000
gtgtcacaag aggttcgtgt ctgtccaggt cgtggctata tccttcgtgt tacagcgtac    3060
aaagagggat atggagaagg ttgcgtaacg atccatgaga tcgagaacaa tacagacgaa    3120
ctgaaattca caactgtgt agaagaggaa gtatatccaa acaacacggt aacgtgtatt    3180
aattatactg cgactcaaga gaatatgag ggtacgtaca cttctcgtaa tcgaggatat    3240
gacgaagcct atggtaataa cccttccgta ccagctgatt atgcgtcagt ctatgaagaa    3300
aaatcgtata cagatagacg aagagagaat ccttgtgaat ctaacagagg atatggagat    3360
tacacaccac taccagctgg ttatgtaaca aaggaattag agtacttccc agagaccgat    3420
aaggtatgga ttgagattgg agaaacagaa ggaacattca tcgtggacag cgtggaatta    3480
ctccttatgg aggaa                                                    3495
```

<210> SEQ ID NO 4
<211> LENGTH: 1165
<212> TYPE: PRT
<213> ORGANISM: Bacillus thuringiensis

<400> SEQUENCE: 4

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110
```

```
Phe Ser Asp Trp Glu Lys Asp Pro Thr Asn Pro Ala Leu Arg Glu Glu
            115                 120                 125
Met Arg Ile Gln Phe Asn Asp Met Asn Ser Ala Leu Ile Thr Ala Ile
        130                 135                 140
Pro Leu Phe Arg Val Gln Asn Tyr Glu Val Ala Leu Leu Ser Val Tyr
145                 150                 155                 160
Val Gln Ala Ala Asn Leu His Leu Ser Ile Leu Arg Asp Val Ser Val
                165                 170                 175
Phe Gly Glu Arg Trp Gly Tyr Asp Thr Ala Thr Ile Asn Asn Arg Tyr
            180                 185                 190
Ser Asp Leu Thr Ser Leu Ile His Val Tyr Thr Asn His Cys Val Asp
        195                 200                 205
Thr Tyr Asn Gln Gly Leu Arg Leu Glu Gly Arg Phe Leu Ser Asp
            210                 215                 220
Trp Ile Val Tyr Asn Arg Phe Arg Arg Gln Leu Thr Ile Ser Val Leu
225                 230                 235                 240
Asp Ile Val Ala Phe Phe Pro Asn Tyr Asp Ile Arg Thr Tyr Pro Ile
                245                 250                 255
Gln Thr Ala Thr Gln Leu Thr Arg Glu Val Tyr Leu Asp Leu Pro Phe
            260                 265                 270
Ile Asn Glu Asn Leu Ser Pro Ala Ala Ser Tyr Pro Thr Phe Ser Ala
        275                 280                 285
Ala Glu Ser Ala Ile Ile Arg Ser Pro His Leu Val Asp Phe Leu Asn
            290                 295                 300
Ser Phe Thr Ile Tyr Thr Asp Ser Leu Ala Arg Tyr Ala Tyr Trp Gly
305                 310                 315                 320
Gly His Leu Val Asn Ser Phe Arg Thr Gly Thr Thr Asn Leu Ile
                325                 330                 335
Arg Ser Pro Leu Tyr Gly Arg Glu Gly Asn Thr Glu Arg Pro Val Thr
            340                 345                 350
Ile Thr Ala Ser Pro Ser Val Pro Ile Phe Arg Thr Leu Ser Tyr Ile
        355                 360                 365
Thr Gly Leu Asp Asn Ser Asn Pro Val Ala Gly Ile Glu Gly Val Glu
370                 375                 380
Phe Gln Asn Thr Ile Ser Arg Ser Ile Tyr Arg Lys Ser Gly Pro Ile
385                 390                 395                 400
Asp Ser Phe Ser Glu Leu Pro Pro Gln Asp Ala Ser Val Ser Pro Ala
                405                 410                 415
Ile Gly Tyr Ser His Arg Leu Cys His Ala Thr Phe Leu Glu Arg Ile
            420                 425                 430
Ser Gly Pro Arg Ile Ala Gly Thr Val Phe Ser Trp Thr His Arg Ser
        435                 440                 445
Ala Ser Pro Thr Asn Glu Val Ser Pro Ser Arg Ile Thr Gln Ile Pro
        450                 455                 460
Trp Val Lys Ala His Thr Leu Ala Ser Gly Ala Ser Val Ile Lys Gly
465                 470                 475                 480
Pro Gly Phe Thr Gly Gly Asp Ile Leu Thr Arg Asn Ser Met Gly Glu
                485                 490                 495
Leu Gly Thr Leu Arg Val Thr Phe Thr Gly Arg Leu Pro Gln Ser Tyr
            500                 505                 510
Tyr Ile Arg Phe Arg Tyr Ala Ser Val Ala Asn Arg Ser Gly Thr Phe
        515                 520                 525
```

```
Arg Tyr Ser Gln Pro Pro Ser Tyr Gly Ile Ser Phe Pro Lys Thr Met
    530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
            565                 570                 575

Ile Gln Ser Gly Val Tyr Ile Asp Arg Ile Glu Phe Ile Pro Val Thr
            580                 585                 590

Ala Thr Phe Glu Ala Glu Tyr Asp Leu Glu Arg Ala Gln Lys Val Val
        595                 600                 605

Asn Ala Leu Phe Thr Ser Thr Asn Gln Leu Gly Leu Lys Thr Asp Val
    610                 615                 620

Thr Asp Tyr His Ile Asp Gln Val Ser Asn Leu Val Ala Cys Leu Ser
625                 630                 635                 640

Asp Glu Phe Cys Leu Asp Glu Lys Arg Glu Leu Ser Glu Lys Val Lys
            645                 650                 655

His Ala Lys Arg Leu Ser Asp Glu Arg Asn Leu Leu Gln Asp Pro Asn
        660                 665                 670

Phe Arg Gly Ile Asn Arg Gln Pro Asp Arg Gly Trp Arg Gly Ser Thr
    675                 680                 685

Asp Ile Thr Ile Gln Gly Gly Asp Asp Val Phe Lys Glu Asn Tyr Val
690                 695                 700

Thr Leu Pro Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
            725                 730                 735

Gly Tyr Ile Glu Asp Ser Gln Asp Leu Glu Ile Tyr Leu Ile Arg Tyr
        740                 745                 750

Asn Ala Lys His Glu Ile Val Asn Val Pro Gly Thr Gly Ser Leu Trp
    755                 760                 765

Pro Leu Ser Val Glu Asn Gln Ile Gly Pro Cys Gly Glu Pro Asn Arg
770                 775                 780

Cys Ala Pro His Leu Glu Trp Asn Pro Asp Leu His Cys Ser Cys Arg
785                 790                 795                 800

Asp Gly Glu Lys Cys Ala His His Ser His His Phe Ser Leu Asp Ile
            805                 810                 815

Asp Val Gly Cys Thr Asp Leu Asn Glu Asp Leu Gly Val Trp Val Ile
        820                 825                 830

Phe Lys Ile Lys Thr Gln Asp Gly His Ala Arg Leu Gly Asn Leu Glu
    835                 840                 845

Phe Leu Glu Glu Lys Pro Leu Leu Gly Glu Ala Leu Ala Arg Val Lys
850                 855                 860

Arg Ala Glu Lys Lys Trp Arg Asp Lys Arg Glu Thr Leu Gln Leu Glu
865                 870                 875                 880

Thr Thr Ile Val Tyr Lys Glu Ala Lys Glu Ser Val Asp Ala Leu Phe
            885                 890                 895

Val Asn Ser Gln Tyr Asp Arg Leu Gln Ala Asp Thr Asn Ile Ala Met
        900                 905                 910

Ile His Ala Ala Asp Lys Arg Val His Arg Ile Arg Glu Ala Tyr Leu
    915                 920                 925

Pro Glu Leu Ser Val Ile Pro Gly Val Asn Ala Ala Ile Phe Glu Glu
930                 935                 940

Leu Glu Glu Arg Ile Phe Thr Ala Phe Ser Leu Tyr Asp Ala Arg Asn
```

-continued

```
                945           950            955            960
        Ile Ile Lys Asn Gly Asp Phe Asn Asn Gly Leu Leu Cys Trp Asn Val
                    965            970            975
        Lys Gly His Val Glu Val Glu Glu Gln Asn Asn His Arg Ser Val Leu
                    980            985            990
        Val Ile Pro Glu Trp Glu Ala Glu  Val Ser Gln Glu Val  Arg Val Cys
                995            1000           1005
        Pro Gly Arg Gly Tyr Ile Leu  Arg Val Thr Ala Tyr  Lys Glu Gly
                1010           1015           1020
        Tyr Gly Glu Gly Cys Val Thr  Ile His Glu Ile Glu  Asn Asn Thr
                1025           1030           1035
        Asp Glu Leu Lys Phe Asn Asn  Cys Val Glu Glu Glu  Val Tyr Pro
                1040           1045           1050
        Asn Asn Thr Val Thr Cys Ile  Asn Tyr Thr Ala Thr  Gln Glu Glu
                1055           1060           1065
        Tyr Glu Gly Thr Tyr Thr Ser  Arg Asn Arg Gly Tyr  Asp Glu Ala
                1070           1075           1080
        Tyr Gly Asn Asn Pro Ser Val  Pro Ala Asp Tyr Ala  Ser Val Tyr
                1085           1090           1095
        Glu Glu Lys Ser Tyr Thr Asp  Arg Arg Arg Glu Asn  Pro Cys Glu
                1100           1105           1110
        Ser Asn Arg Gly Tyr Gly Asp  Tyr Thr Pro Leu Pro  Ala Gly Tyr
                1115           1120           1125
        Val Thr Lys Glu Leu Glu Tyr  Phe Pro Glu Thr Asp  Lys Val Trp
                1130           1135           1140
        Ile Glu Ile Gly Glu Thr Glu  Gly Thr Phe Ile Val  Asp Ser Val
                1145           1150           1155
        Glu Leu Leu Leu Met Glu Glu
                1160           1165

<210> SEQ ID NO 5
<211> LENGTH: 3567
<212> TYPE: DNA
<213> ORGANISM: Bacillus thuringiensis

<400> SEQUENCE: 5
atggaggaaa ataatcaaaa tcaatgcata ccttacaatt gtttaagtaa tcctgaagaa      60
gtacttttgg atggagaacg gatatcaact ggtaattcat caattgatat ttctctgtca     120
cttgttcagt ttctggtatc taactttgta ccagggggag attttttagt tggattaata     180
gattttgtat ggggaatagt tggcccttct caatgggatg catttctagt acaaattgaa     240
caattaatta tgaaagaat  agctgaattt gctaggaatg ctgctattgc taatttagaa     300
ggattaggaa acaatttcaa tatatatgtg gaagcattta agaatgggag aagatcct      360 aataatccag caaccaggac cagagtaatt gatcgctttc gtatacttga tgggctactt     420
gaaagggaca ttccttcgtt tcgaatttct ggatttgaag taccccttttt atccgtttat     480 gctcaagcgg ccaatctgca tctagctata ttaagagatt ctgtaatttt tggagaaaga     540
tggggattga acgataaa tgtcaatgaa actataata gactaattag gcatattgat     600
gaatatgctg atcactgtgc aaatacgtat aatcggggat aaataatttt accgaaatct     660
acgtatcaag attggataac atataatcga ttacggagag acttaacatt gactgtatta     720
gatatcgccg ctttctttcc aaactatgac aataggagat atccaattca gccagttggt     780
caactaacaa gggaagttta tacggaccca ttaattaatt ttaatccaca gttacagtct     840
```

```
gtagctcaat tacctacttt taacgttatg gagagcagcg caattagaaa tcctcattta    900
tttgatatat tgaataatct tacaatcttt acggattggt ttagtgttgg acgcaatttt    960
tattggggag gacatcgagt aatatctagc cttataggag gtggtaacat aacatctcct   1020
atatatggaa gagaggcgaa ccaggagcct ccaagatcct ttacttttaa tggaccggta   1080
tttaggactt tatcaaatcc tactttacga ttattacagc aaccttggcc agcgccacca   1140
tttaatttac gtggtgttga aggagtagaa ttttctacac ctacaaatag ctttacgtat   1200
cgaggaagag gtcaggttga ttctttaact gaattaccgc ctgaggataa tagtgtgcca   1260
cctcgcgaag gatatagtca tcgtttatgt catgcaactt ttgttcaaag atctggaaca   1320
ccttttttaa caactggtgt agtattttct tggacgcatc gtagtgcaac tcttacaaat   1380
acaattgatc cagagagaat taatcaaata cctttagtga aaggatttag agtttggggg   1440
ggcacctctg tcattacagg accaggattt acaggagggg atatccttcg aagaaatacc   1500
tttggtgatt ttgtatctct acaagtcaat attaattcac caattaccca agataccgt   1560
ttaagatttc gttacgcttc cagtagggat gcacgagtta tagtattaac aggagcggca   1620
tccacaggag tgggaggcca agttagtgta aatatgcctc ttcagaaaac tatggaaata   1680
ggggagaact taacatctag aacatttaga tataccgatt ttagtaatcc ttttcatt    1740
agagctaatc cagatataat tgggataagt gaacaacctc tatttggtgc aggttctatt   1800
agtagcggtg aactttatat agataaaatt gaaattattc tagcagatgc aacatttgaa   1860
gcagaatctg atttagaaag agcacaaaag gcggtgaatg ccctgtttac ttcttccaat   1920
caaatcgggt taaaaaccga tgtgacggat tatcatattg atcaagtatc caatttagtg   1980
gattgtttat cagatgaatt ttgtctggat gaaaagcgag aattgtccga aaagtcaaa   2040
catgcgaagc gactcagtga tgagcggaat ttacttcaag atccaaactt cagagggatc   2100
aatagacaac cagaccgtgg ctggagagga agtacagata ttaccatcca aggaggagat   2160
gacgtattca aagagaatta cgtcacacta ccgggtaccg ttgatgagtg ctatccaacg   2220
tatttatatc agaaaataga tgagtcgaaa ttaaaagctt atacccgtta tgaattaaga   2280
gggtatatcg aagatagtca agacttagaa atctatttga tccgttacaa tgcaaaacac   2340
gaaatagtaa atgtgccagg cacgggttcc ttatggccgc tttcagccca agtccaatc    2400
ggaaagtgtg gagaaccgaa tcgatgcgcg ccacaccttg aatggaatcc tgatctagat   2460
tgttcctgca gagacgggga aaaatgtgca catcattccc atcatttcac cttggatatt   2520
gatgttggat gtacagactt aaatgaggac ttaggtctat gggtgatatt caagattaag   2580
acgcaagata accatgcaag actagggaat ctagagtttc tcgaagagaa accattatta   2640
ggggaagcac tagctcgtgt gaaaagagcg gagaagaagt ggagagacaa acgagagaaa   2700
ctgcagttgg aaacaaatat tgtttataaa gaggcaaaag aatctgtaga tgctttattt   2760
gtaaactctc aatatgatag attacaagtg aatacgaaca tcgcaatgat tcatgcggca   2820
gataaacgcg ttcatagaat ccgggaagcg tatctgccag agttgtctgt gattccaggt   2880
gtcaatgcgg ccattttcga agaattagag ggacgtattt ttacagcgta ttccttatat   2940
gatgcgagaa atgtcattaa aaatggcgat tcaataatg gcttattatg ctggaacgtg    3000
aaaggtcatg tagatgtaga agagcaaaac aaccaccgtt cggtccttgt tatcccagaa   3060
tgggaggcag aagtgtcaca agaggttcgt gtctgtccag gtcgtggcta tatccttcgt   3120
gtcacagcat ataagagggg atatggagag ggctgcgtaa cgatccatga gatcgaagac   3180
```

-continued

```
aatacagacg aactgaaatt cagcaactgt gtagaagagg aagtatatcc aaacaacaca    3240
gtaacgtgta ataattatac tgggactcaa gaagaatatg agggtacgta cacttctcgt    3300
aatcaaggat atgacgaagc ctatggtaat aacccttccg taccagctga ttacgcttca    3360
gtctatgaag aaaaatcgta tacagatgga cgaagagaga tccttgtga atctaacaga    3420 ggctatgggg attacacacc actaccggct ggttatgtaa caaaggattt agagtacttc    3480
ccagagaccg ataaggtatg gattgagatc ggagaaacag aaggaacatt catcgtggat    3540
agcgtggaat tactccttat ggaggaa                                       3567
```

<210> SEQ ID NO 6
<211> LENGTH: 1189
<212> TYPE: PRT
<213> ORGANISM: Bacillus thuringiensis

<400> SEQUENCE: 6

```
Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300
```

```
Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Gln Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
```

-continued

```
                725                 730                 735
Cys Tyr Pro Thr Tyr Leu Tyr Gln Lys Ile Asp Glu Ser Lys Leu Lys
            740                 745                 750
Ala Tyr Thr Arg Tyr Glu Leu Arg Gly Tyr Ile Glu Asp Ser Gln Asp
            755                 760                 765
Leu Glu Ile Tyr Leu Ile Arg Tyr Asn Ala Lys His Glu Ile Val Asn
            770                 775                 780
Val Pro Gly Thr Gly Ser Leu Trp Pro Leu Ser Ala Gln Ser Pro Ile
785                 790                 795                 800
Gly Lys Cys Gly Glu Pro Asn Arg Cys Ala Pro His Leu Glu Trp Asn
            805                 810                 815
Pro Asp Leu Asp Cys Ser Cys Arg Asp Gly Glu Lys Cys Ala His His
            820                 825                 830
Ser His His Phe Thr Leu Asp Ile Asp Val Gly Cys Thr Asp Leu Asn
            835                 840                 845
Glu Asp Leu Gly Leu Trp Val Ile Phe Lys Ile Lys Thr Gln Asp Asn
            850                 855                 860
His Ala Arg Leu Gly Asn Leu Glu Phe Leu Glu Glu Lys Pro Leu Leu
865                 870                 875                 880
Gly Glu Ala Leu Ala Arg Val Lys Arg Ala Glu Lys Lys Trp Arg Asp
            885                 890                 895
Lys Arg Glu Lys Leu Gln Leu Glu Thr Asn Ile Val Tyr Lys Glu Ala
            900                 905                 910
Lys Glu Ser Val Asp Ala Leu Phe Val Asn Ser Gln Tyr Asp Arg Leu
            915                 920                 925
Gln Val Asn Thr Asn Ile Ala Met Ile His Ala Ala Asp Lys Arg Val
            930                 935                 940
His Arg Ile Arg Glu Ala Tyr Leu Pro Glu Leu Ser Val Ile Pro Gly
945                 950                 955                 960
Val Asn Ala Ala Ile Phe Glu Glu Leu Glu Gly Arg Ile Phe Thr Ala
            965                 970                 975
Tyr Ser Leu Tyr Asp Ala Arg Asn Val Ile Lys Asn Gly Asp Phe Asn
            980                 985                 990
Asn Gly Leu Leu Cys Trp Asn Val Lys Gly His Val Asp Val Glu Glu
            995                 1000                1005
Gln Asn Asn His Arg Ser Val Leu Val Ile Pro Glu Trp Glu Ala
            1010                1015                1020
Glu Val Ser Gln Glu Val Arg Val Cys Pro Gly Arg Gly Tyr Ile
            1025                1030                1035
Leu Arg Val Thr Ala Tyr Lys Glu Gly Tyr Gly Glu Gly Cys Val
            1040                1045                1050
Thr Ile His Glu Ile Glu Asp Asn Thr Asp Glu Leu Lys Phe Ser
            1055                1060                1065
Asn Cys Val Glu Glu Glu Val Tyr Pro Asn Asn Thr Val Thr Cys
            1070                1075                1080
Asn Asn Tyr Thr Gly Thr Gln Glu Glu Tyr Glu Gly Thr Tyr Thr
            1085                1090                1095
Ser Arg Asn Gln Gly Tyr Asp Glu Ala Tyr Gly Asn Asn Pro Ser
            1100                1105                1110
Val Pro Ala Asp Tyr Ala Ser Val Tyr Glu Glu Lys Ser Tyr Thr
            1115                1120                1125
Asp Gly Arg Arg Glu Asn Pro Cys Glu Ser Asn Arg Gly Tyr Gly
            1130                1135                1140
```

-continued

```
Asp Tyr Thr Pro Leu Pro Ala Gly Tyr Val Thr Lys Asp Leu Glu
    1145                1150                1155

Tyr Phe Pro Glu Thr Asp Lys Val Trp Ile Glu Ile Gly Glu Thr
    1160                1165                1170

Glu Gly Thr Phe Ile Val Asp Ser Val Glu Leu Leu Leu Met Glu
    1175                1180                1185

Glu

<210> SEQ ID NO 7
<211> LENGTH: 3522
<212> TYPE: DNA
<213> ORGANISM: Bacillus thuringiensis

<400> SEQUENCE: 7
```

| | | | | | |
|---|---|---|---|---|---|
| atggagaata | tattcaaaa | tcaatgcgta | ccttacaatt | gtttaaataa | tcctgaagta | 60 |
| gaaatattaa | atgaagaaag | aagtactggc | agattaccgt | tagatatatc | cttatcgctt | 120 |
| acacgtttcc | ttttgagtga | atttgttcca | ggtgtgggag | ttgcgtttgg | attatttgat | 180 |
| ttaatatggg | gttttataac | tccttctgat | tggagcttat | ttcttttaca | gattgaacaa | 240 |
| ttgattgagc | aaagaataga | aacattggaa | aggaaccggg | caattactac | attacgaggg | 300 |
| ttagcagata | gctatgaaat | ttatattgaa | gcactaagag | agtgggaagc | aaatcctaat | 360 |
| aatgcacaat | taagggaaga | tgtgcgtatt | cgatttgcta | atacagacga | cgctttaata | 420 |
| acagcaataa | ataattttac | acttacaagt | tttgaaatcc | ctcttttatc | ggtctatgtt | 480 |
| caagcggcga | atttacattt | atcactatta | agagacgctg | tatcgtttgg | gcagggttgg | 540 |
| ggactggata | tagctactgt | taataatcat | tataatagat | aataaatct | tattcataga | 600 |
| tatcgaaac | attgtttgga | cacatacaat | caaggattag | aaaacttaag | aggtactaat | 660 |
| actcgacaat | gggcaagatt | caatcagttt | aggagagatt | taacacttac | tgtattagat | 720 |
| atcgttgctc | ttttttccgaa | ctacgatgtt | agaacatatc | caattcaaac | gtcatcccaa | 780 |
| ttaacaaggg | aaatttatac | aagttcagta | attgaggatt | ctccagtttc | tgctaatata | 840 |
| cctaatggtt | taatagggc | ggaatttgga | gttagaccgc | cccatcttat | ggactttatg | 900 |
| aattctttgt | ttgtaactgc | agagactgtt | agaagtcaaa | ctgtgtgggg | aggacactta | 960 |
| gttagttcac | gaaatacggc | tggtaaccgt | ataaatttcc | ctagttacgg | ggtcttcaat | 1020 |
| cctggtggcg | ccatttggat | tgcagatgag | gatccacgtc | ttttttatcg | gacattatca | 1080 |
| gatcctgttt | ttgtccgagg | aggatttggg | aatcctcatt | atgtactggg | gcttagggga | 1140 |
| gtagcatttc | aacaaactgg | tacgaaccac | acccgaacat | ttagaaatag | tgggaccata | 1200 |
| gattctctag | atgaaatccc | acctcaggat | aatagtgggg | caccttggaa | tgattatagt | 1260 |
| catgtattaa | atcatgttac | atttgtacga | tggccaggtg | agatttcagg | aagtgattca | 1320 |
| tggagagctc | caatgttttc | ttggacgcac | cgtagtgcaa | ccectacaaa | tacaattgat | 1380 |
| ccggagagga | ttactcaaat | accattggta | aaagcacata | cacttcagtc | aggtactact | 1440 |
| gttgtaagag | ggcccggtt | tacgggagga | gatattcttc | gacgaacaag | tggaggacca | 1500 |
| tttgcttata | ctattgttaa | tataaatggg | caattacccc | aaaggtatcg | tgcaagaata | 1560 |
| cgctatgcct | ctactacaaa | tctaagaatt | tacgtaacgg | ttgcaggtga | acggattttt | 1620 |
| gctggtcaat | ttaacaaaac | aatggatacc | ggtgacccat | taacattcca | atcttttagt | 1680 |
| tacgcaacta | ttaatacagc | ttttacattc | ccaatgagcc | agagtagttt | cacagtaggt | 1740 |
| gctgatactt | ttagttcagg | gaatgaagtt | tatatagaca | gatttgaatt | gattccagtt | 1800 |

```
actgcaacat tgaagcaga atatgattta gaaagagcac aaaaggcggt gaatgcgctg    1860
tttacttcta taaaccaaat agggataaaa acagatgtga cggattatca tattgatcaa    1920
gtatccaatt tagtggattg tttatcagat gaattttgtc tggatgaaaa gcgagaattg    1980
tccgagaaag tcaaacatgc gaagcgactc agtgatgagc ggaatttact tcaagatcca    2040
aacttcaaag gcatcaatag gcaactagac cgtggttgga gaggaagtac ggatattacc    2100
atccaaagag gagatgacgt attcaaagaa aattatgtca cactaccagg taccttttgat   2160 gagtgctatc caacgtattt atatcaaaaa atagatgagt cgaaattaaa accctatact    2220
cgttatcaat aagagggta tatcgaggat agtcaagact tagaaatcta tttgatccgc     2280
tataatgcaa aacacgaaac agtaaatgtg ctaggtacgg ttctttatg ccgctttca      2340 gtccaaagtc caatcagaaa gtgtggagaa ccgaatcgat gcgcgccaca ccttgaatgg    2400
aatcctgatc tagattgttc ctgcagagac ggggaaaaat gtgcacatca ttcgcatcat    2460
ttctccttgg acattgatgt tggatgtaca gacttaaatg aggacttaga tgtatgggtg    2520
atattcaaga ttaagacgca agatggccat gcaagactag gaaatctaga gtttctcgaa    2580
gagaaaccat tagtcgggga agcactagct cgtgtgaaaa gagcagagaa aaaatggaga    2640
gataaacgtg aaaaattgga attggaaaca aatattgttt ataaagaggc aaaagaatct    2700
gtagatgctt tatttgtaaa ctctcaatat gatcaattac aagcggatac gaatattgcc    2760
atgattcatg cggcagataa acgtgttcat agaattcggg aagcgtatct tccagagtta    2820
tctgtgattc cgggtgtaaa tgtagacatt ttcgaagaat taaagggcg tattttcact     2880 gcattcttcc tatatgatgc gagaaatgtc attaaaaacg gtgatttcaa taatggctta    2940
tcatgctgga acgtgaaagg gcatgtagat gtagaagaac aaaacaacca ccgttcggtc    3000
cttgttgttc cggaatggga agcagaagtg tcacaagaag ttcgtgtctg tccgggtcgt    3060
ggctatatcc ttcgtgtcac agcgtacaag gagggatatg gagaaggttg cgtaaccatt    3120
catgagatcg agaacaatac agacgaactg aagtttagca actgcgtaga gaggaagtc    3180 tatccaaaca cacggtaac gtgtaatgat tatactgcaa atcaagaaga atacggggt     3240 gcgtacactt cccgtaatcg tggatatgac gaaacttatg aagcaattc ttctgtacca    3300 gctgattatg cgtcagtcta tgaagaaaaa tcgtatacag atggacgaag agacaatcct   3360
tgtgaatcta acagaggata tggggattac acaccactac cagctggcta tgtgacaaaa    3420
gaattagagt acttcccaga aaccgataag gtatggattg agatcggaga aacggaagga    3480
acattcatcg tggacagcgt ggaattactc cttatggagg aa                       3522
```

<210> SEQ ID NO 8
<211> LENGTH: 1174
<212> TYPE: PRT
<213> ORGANISM: Bacillus thuringiensis

<400> SEQUENCE: 8

Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

-continued

```
Phe Ile Thr Pro Ser Asp Trp Ser Leu Phe Leu Gln Ile Glu Gln
 65                  70                  75                  80

Leu Ile Glu Gln Arg Ile Glu Thr Leu Glu Arg Asn Arg Ala Ile Thr
                 85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
```

-continued

```
                485                 490                 495
Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
            515                 520                 525

Arg Ile Tyr Val Thr Val Ala Gly Glu Arg Ile Phe Ala Gly Gln Phe
            530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
            595                 600                 605

Asp Leu Glu Arg Ala Gln Lys Ala Val Asn Ala Leu Phe Thr Ser Ile
610                 615                 620

Asn Gln Ile Gly Ile Lys Thr Asp Val Thr Asp Tyr His Ile Asp Gln
625                 630                 635                 640

Val Ser Asn Leu Val Asp Cys Leu Ser Asp Glu Phe Cys Leu Asp Glu
                645                 650                 655

Lys Arg Glu Leu Ser Glu Lys Val Lys His Ala Lys Arg Leu Ser Asp
            660                 665                 670

Glu Arg Asn Leu Leu Gln Asp Pro Asn Phe Lys Gly Ile Asn Arg Gln
            675                 680                 685

Leu Asp Arg Gly Trp Arg Gly Ser Thr Asp Ile Thr Ile Gln Arg Gly
            690                 695                 700

Asp Asp Val Phe Lys Glu Asn Tyr Val Thr Leu Pro Gly Thr Phe Asp
705                 710                 715                 720

Glu Cys Tyr Pro Thr Tyr Leu Tyr Gln Lys Ile Asp Glu Ser Lys Leu
                725                 730                 735

Lys Pro Tyr Thr Arg Tyr Gln Leu Arg Gly Tyr Ile Glu Asp Ser Gln
            740                 745                 750

Asp Leu Glu Ile Tyr Leu Ile Arg Tyr Asn Ala Lys His Glu Thr Val
            755                 760                 765

Asn Val Leu Gly Thr Gly Ser Leu Trp Pro Leu Ser Val Gln Ser Pro
770                 775                 780

Ile Arg Lys Cys Gly Glu Pro Asn Arg Cys Ala Pro His Leu Glu Trp
785                 790                 795                 800

Asn Pro Asp Leu Asp Cys Ser Cys Arg Asp Gly Glu Lys Cys Ala His
                805                 810                 815

His Ser His His Phe Ser Leu Asp Ile Asp Val Gly Cys Thr Asp Leu
            820                 825                 830

Asn Glu Asp Leu Asp Val Trp Val Ile Phe Lys Ile Lys Thr Gln Asp
            835                 840                 845

Gly His Ala Arg Leu Gly Asn Leu Glu Phe Leu Glu Glu Lys Pro Leu
            850                 855                 860

Val Gly Glu Ala Leu Ala Arg Val Lys Arg Ala Glu Lys Lys Trp Arg
865                 870                 875                 880

Asp Lys Arg Glu Lys Leu Glu Leu Glu Thr Asn Ile Val Tyr Lys Glu
                885                 890                 895

Ala Lys Glu Ser Val Asp Ala Leu Phe Val Asn Ser Gln Tyr Asp Gln
            900                 905                 910
```

```
Leu Gln Ala Asp Thr Asn Ile Ala Met Ile His Ala Ala Asp Lys Arg
        915                 920                 925

Val His Arg Ile Arg Glu Ala Tyr Leu Pro Glu Leu Ser Val Ile Pro
        930                 935                 940

Gly Val Asn Val Asp Ile Phe Glu Leu Lys Gly Arg Ile Phe Thr
945                 950                 955                 960

Ala Phe Phe Leu Tyr Asp Ala Arg Asn Val Ile Lys Asn Gly Asp Phe
                965                 970                 975

Asn Asn Gly Leu Ser Cys Trp Asn Val Lys Gly His Val Asp Val Glu
        980                 985                 990

Glu Gln Asn Asn His Arg Ser Val Leu Val Val Pro Glu Trp Glu Ala
        995                 1000                1005

Glu Val  Ser Gln Glu Val  Arg Val Cys Pro Gly Arg  Gly Tyr Ile
    1010                 1015                1020

Leu Arg  Val Thr Ala Tyr  Lys Glu Gly Tyr Gly Glu  Gly Cys Val
    1025                 1030                1035

Thr Ile  His Glu Ile Glu  Asn Asn Thr Asp Glu Leu  Lys Phe Ser
    1040                 1045                1050

Asn Cys  Val Glu Glu Val  Tyr Pro Asn Asn Thr  Val Thr Cys
    1055                 1060                1065

Asn Asp  Tyr Thr Ala Asn Gln  Glu Glu Tyr Gly  Ala Tyr Thr
    1070                 1075                1080

Ser Arg  Asn Arg Gly Tyr Asp  Glu Thr Tyr Gly Ser  Asn Ser Ser
    1085                 1090                1095

Val Pro  Ala Asp Tyr Ala Ser  Val Tyr Glu Glu Lys  Ser Tyr Thr
    1100                 1105                1110

Asp Gly  Arg Arg Asp Asn Pro  Cys Glu Ser Asn Arg  Gly Tyr Gly
    1115                 1120                1125

Asp Tyr  Thr Pro Leu Pro Ala  Gly Tyr Val Thr Lys  Glu Leu Glu
    1130                 1135                1140

Tyr Phe  Pro Glu Thr Asp Lys  Val Trp Ile Glu Ile  Gly Glu Thr
    1145                 1150                1155

Glu Gly  Thr Phe Ile Val Asp  Ser Val Glu Leu Leu  Leu Met Glu
    1160                 1165                1170

Glu

<210> SEQ ID NO 9
<211> LENGTH: 42
<212> TYPE: DNA
<213> ORGANISM: Artificial Sequence
<220> FEATURE:
<223> OTHER INFORMATION: 42-mer oligonucleotide constructed to the
      sequence of the insert in pM2,31-4

<400> SEQUENCE: 9
ggataccggt gacccattaa cattccaatc ttttagttac gc                        42

<210> SEQ ID NO 10
<211> LENGTH: 40
<212> TYPE: DNA
<213> ORGANISM: Artificial Sequence
<220> FEATURE:
```

```
<223> OTHER INFORMATION: 40-mer oligonucleotide constructed to the
      sequence of the insert in pM2,31-1

<400> SEQUENCE: 10
gaagtttatg gcctctttct gtagaaaatc aaattggacc                              40
```